United States Patent [19]
Leach et al.

[11] Patent Number: 5,505,721
[45] Date of Patent: Apr. 9, 1996

[54] MULTIPLE TUBE PERFUSION SAMPLER

[76] Inventors: Gregory L. Leach, 405 Royal Crest Dr., Rice Lake, 548; Albert C. Phelps, 1121 Florence Ave., Eau Claire, 547; Mark L. Krebs, 315 Royal Crest Dr., Rice Lake, Wis. 54868

[21] Appl. No.: 122,930

[22] Filed: Sep. 16, 1993

[51] Int. Cl.$^6$ .................................................. A61B 19/00
[52] U.S. Cl. ................ 604/403; 604/407; 604/411; 604/412; 604/414; 604/415; 604/257; 604/272; 128/762; 128/763; 128/764; 128/766
[58] Field of Search ................... 128/760, 762, 128/763, 764, 766; 604/257–258, 272–273, 317, 403, 407, 411–415, 191, 82

[56] References Cited

U.S. PATENT DOCUMENTS

| | | |
|---|---|---|
| 2,460,641 | 2/1949 | Kleiner . |
| 3,405,706 | 10/1968 | Cinqualbre ............................. 128/762 |
| 3,494,351 | 2/1970 | Horn ..................................... 128/762 |
| 3,604,410 | 9/1971 | Whitacre ............................... 128/762 |
| 3,696,806 | 10/1972 | Sausse ................................... 128/762 |
| 3,733,439 | 1/1973 | McDonald . |
| 3,848,581 | 11/1974 | Cinqualbre et al. ................... 128/766 |
| 3,877,465 | 4/1975 | Miyake . |
| 4,434,802 | 3/1984 | Rilliet . |
| 4,492,634 | 1/1985 | Villa-Real . |
| 4,676,256 | 6/1987 | Golden .................................. 128/763 |
| 4,703,762 | 11/1987 | Rathbone et al. . |
| 4,951,685 | 8/1990 | Blair . |
| 4,976,271 | 12/1990 | Blair . |
| 5,033,476 | 7/1991 | Kasai . |
| 5,086,780 | 2/1992 | Schmidt . |
| 5,104,375 | 4/1992 | Wolf et al. ............................ 604/56 |
| 5,314,412 | 5/1994 | Rex ....................................... 604/191 |
| 5,360,423 | 11/1994 | McCormick ......................... 604/403 |

Primary Examiner—Randall L. Green
Assistant Examiner—P. Zuttarelli
Attorney, Agent, or Firm—Hugh D. Jaeger

[57] ABSTRACT

An apparatus for withdrawing blood from a vein and simultaneously filling multiple collection tubes. The apparatus includes a movable sheath which protects the technician from inadvertently contacting the withdrawn needle after use and a laminar flow transition chamber between the blood withdrawal needle and the multiple collection tubes.

12 Claims, 12 Drawing Sheets

MULTIPLE TUBE PERFUSION SAMPLER

BACKGROUND OF THE INVENTION

1. Field of the Invention

This invention relates to an apparatus for withdrawing blood from a vein and simultaneously filling multiple collection tubes. The apparatus includes a movable sheath which protects the technician from inadvertently contacting the withdrawn needle after use and a laminar flow transition chamber between the blood withdrawal needle and the multiple collection tubes.

2. Discussion of the Prior Art

The withdrawal of blood from a vein for the purpose of analysis is customarily done by inserting one end of a double ended hollow needle into a vein and inserting an evacuated collection tube onto the septum protected other end. Analytical laboratory practice dictates that multiple sample tubes be used where more than one test is to be run. The filling of multiple sample tubes is done serially, as one tube fills, it is withdrawn from the double ended needle and another sample tube is inserted onto the septum protected end of the needle. Since even the most common place blood analysis requires that multiple sample tubes be filled, it is the exception where a single tube is filled.

While it is obvious that the serial filling of the sample tube is slower than simultaneous filling of multiple tubes, there are other, more subtle, problems associated with the serial operation. The withdrawal needle must be centrally positioned within the patient's vein to avoid the rupture and destruction of red blood cells due to high velocity contact between the needle and the interior wall of the vein. This can render the blood sample worthless. The difficulty of holding the needle in the proper position is substantially increased when the technician is obliged to hold the assembly with one hand during the time the original sample tube is withdrawn and a new blood sample tube is inserted onto the septum protected end of the needle.

The danger associated with drawing blood samples from a patient is well recognized and certain safeguards have been adopted to protect the patient and the technician who performs the phlebotomy. While single-use sterile needles are normally effective to protect the patient from infectious diseases and reduce the danger to the technician, the needle is still exposed from the time it is withdrawn from the patient until it can be safely disposed of.

Despite the fact that current blood analysis instruments utilize only a small fraction of the quantity in the common sample tube, typically less than 1% of the volume within the tube, the difficulty of manipulating a much smaller tube during the serial filling of multiple tubes has presented a substantial obstacle to any reduction in size. While the actual amount of blood wasted due to the continued use of the large tube is relatively insignificant to the patient, the disposal of the unused blood presents a problem of ever increasing importance to the analytical laboratory for both cost and safety reasons.

The problems presented by a blood sample contaminated with ruptured red blood cells are well recognized and technicians are given training in the techniques which minimize such destruction. Nevertheless, it still occurs with sufficient frequency to be a concern. Even the most careful technician may be unable to prevent the high velocity impact of the blood against the sample tube during the initial phase of the filling procedure. Additionally, in the case where multiple samples are withdrawn from a patient with relatively small or constricted veins, the difficulty of holding the needle in a position away from the vein wall is such that additional sample must be drawn to ensure a sufficient number of samples uncontaminated by ruptured red blood cells.

The various tests performed on the withdrawn blood sample sometimes require that the blood be treated at the time it is withdrawn, for example, the addition of anticoagulants. Since these treatments render the blood unsuitable for other tests, each such treatment requires a discrete sample tube.

Various attempts have been made to solve individual problems discussed above. For example U.S. Pat. No. 4,492,634 discloses a sample collection tube which includes a baffle portion of the elastomeric stopper. The baffle is designed to curtail the potential mechanical hemolysis resulting from high velocity impact of the red blood cells against the wall of the sample tube during the initial inrush of blood.

The blood collection tube described in U.S. Pat. No. 4,434,802 includes a narrow bore primary tube which acts on the jet of bloodgushing from the needle by peripheral lateral attraction to convert the flow into a relatively slow and well controlled flow to reduce the damage caused to red blood cells.

The teaching of U.S. Pat. No. 4,947,863 is directed to protection against accidental needle stick from the collection needle. To this end, an outer sleeve is coaxially positioned over the blood collection tube holder and is adapted to slide over the collection needle.

U.S. Pat. No. 4,703,762 describes a blood sample withdrawing device which has the ability to fill two sample tubes, connected in tandem, from the same puncture. However, this device requires the use of specialized sample tubes which are not evacuated.

The multiple sample blood collection system shown in U.S. Pat. No. 3,933,439 does not allow the use of standard collection tubes but utilizes a highly specialized elastic bellows arrangement which accommodates the later withdrawal of individual samples.

SUMMARY OF THE INVENTION

According to this invention, a blood withdrawal device is provided which has multiple vacuum sample tubes housed within a single blood collection sample tube holder. Each of the vacuum sample tubes fits within a corresponding aperture within the sample tube holder. Individual sample tube filling needles are positioned at the bottom of each sample tube aperture to puncture the plug in the sample tube holder when the sample tubes are pushed into the apertures. The filling needles are connected to the venipuncture needle through a manifold which provides for equal distribution and laminar flow of the blood from the collection needle to the filling needles during the sample collection procedure. A positionable protective sheath around the sample tube holder is adapted to slide out and extend over the venipuncture needle before and/or after the sample collection procedure to protect against inadvertent contact with the venipuncture needle.

It is therefore an object of this invention to provide a device for withdrawing blood from a patient and simultaneously filling multiple sample tubes.

It is another object of this invention to provide a multiple sample tube device which overcomes the manipulation problems normally associated with small sample tubes.

It is still another object of this invention to provide a blood withdrawal device which reduces the destruction of red blood cells due to high velocity impact with the walls of the device or the sample tube.

A further object of this invention is to provide a blood withdrawal device which accommodates the protection of the needle against accidental contact immediately upon withdrawal from the patient, and, still further object of this invention is to reduce the amount of blood for each sample withdrawn from the patient.

A still further object of this invention is to provide greater patient comfort by limiting the time required to sample the patient thereby reducing psychological anxiety and actual physical trauma.

BRIEF DESCRIPTION OF THE DRAWINGS

Other objects of the invention and many of the attendant advantages of the present invention will be readily appreciated as the same becomes better understood by reference to the following detailed description when considered in connection with the accompanying drawings.

DETAILED DESCRIPTION OF THE PREFERRED EMBODIMENTS

Figure 1:
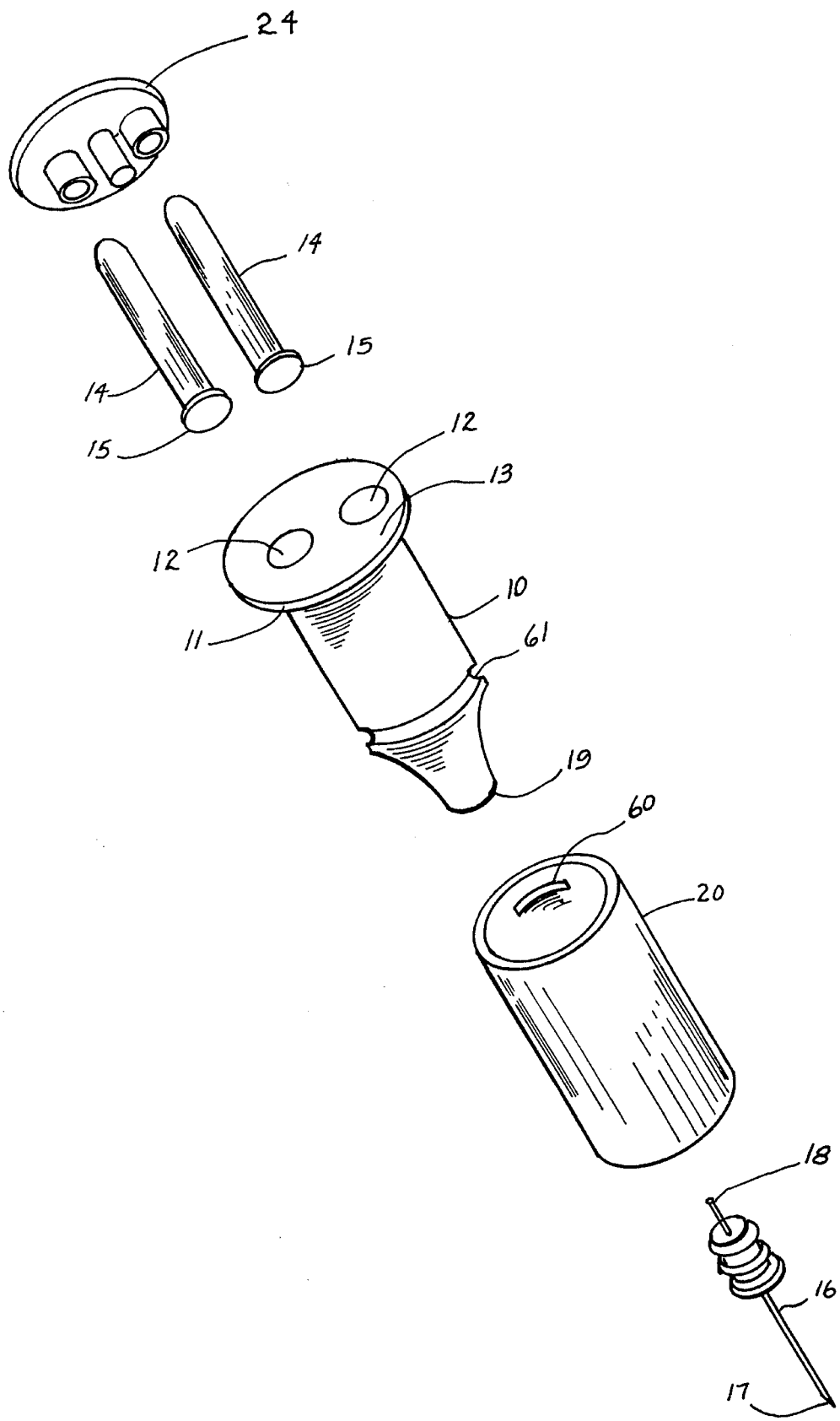
FIG. 1 is a partially exploded view of the blood sample collection device with the multiple blood sample tubes in position to be inserted in the blood sample tube holder.
Figure 2:
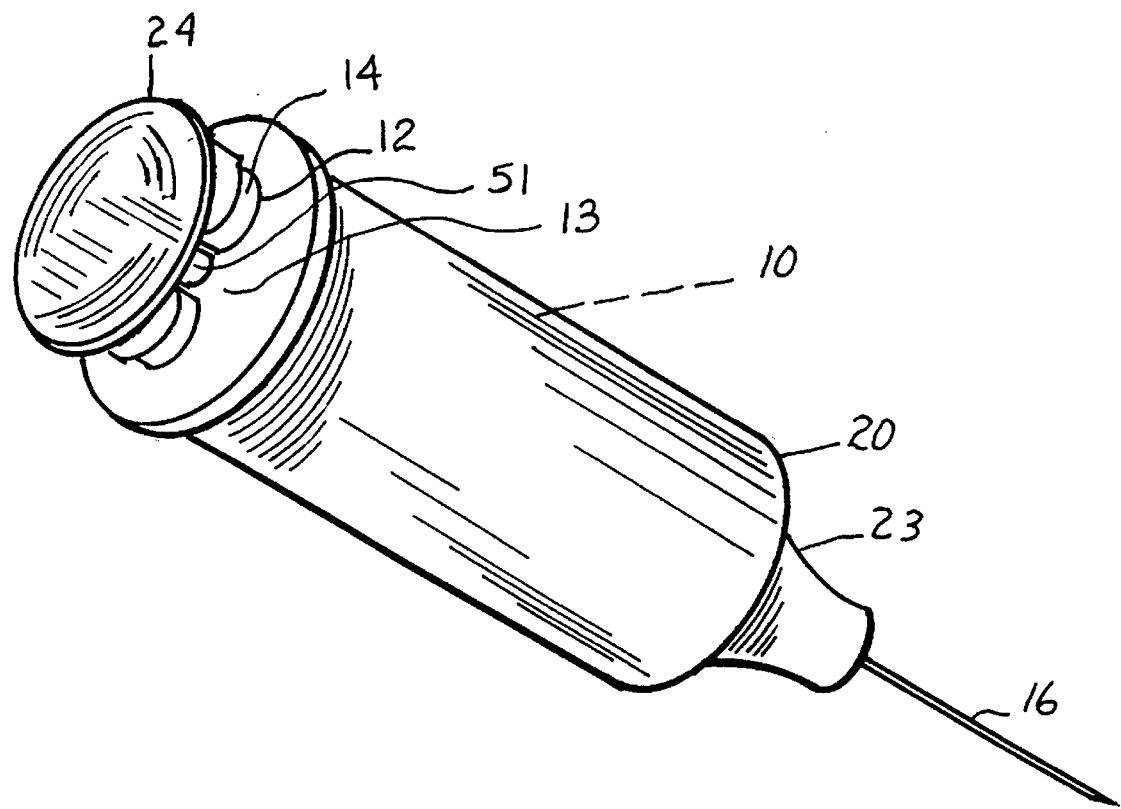
FIG. 2 is a view of the blood sample collection device ready for use.

With reference to FIG. 1, blood sample tube holder 10 includes a plurality of apertures 12a and 12b in the first end 13 for accommodation of blood sample tubes 14a and 14b. A venipuncture needle 16, having a first end 17 for insertion into the patient from whom blood is to be withdrawn and a second end 18 which discharges blood into the blood sample tube holder 10, is affixed to the second end 19 of sample tube holder 10. A movable venipuncture needle sheath 20 aligns over the blood sample tube holder 10 and is shown in the retracted position around blood sample tube holder 10 in FIG. 2. Multiple evacuated blood sample tubes 14a–14b are shown in alignment with the multiple corresponding apertures 12a and 12b in the blood sample tube holder 10. When the device is to be used, the blood sample tubes 14a–14b will be partially inserted into the apertures 12a–12b as shown in FIG. 2. The movable sheath 20 is positioned manually over and about the blood sample tube holder 10. The blood sample tube holder 10 is held by grasping the moveable sheath 20, which is somewhat flexible, and the underlying blood sample tube holder 10 and flange while inserting venipuncture needle 16 into the patient. When the needle 16 is properly positioned, the technician applies pressure to the sample tube loader 24 and forces the blood sample tubes 14a and 14b into the blood sample tube holder 10, as shown in FIG. 2, where the elastomeric stoppers 15a and 15b are punctured by the first end 34a of sample tube filling needles 34 (shown in FIG. 3). The blood then flows smoothly from the second end 18 of venipuncture needle 16, through the distribution manifold 30 into second end 34b of blood sample tube filling needle 34, through blood sample tube filling needles 34 and out first end 34a of filling needles 34 into the evacuated blood sample tubes 14.

Figure 6:
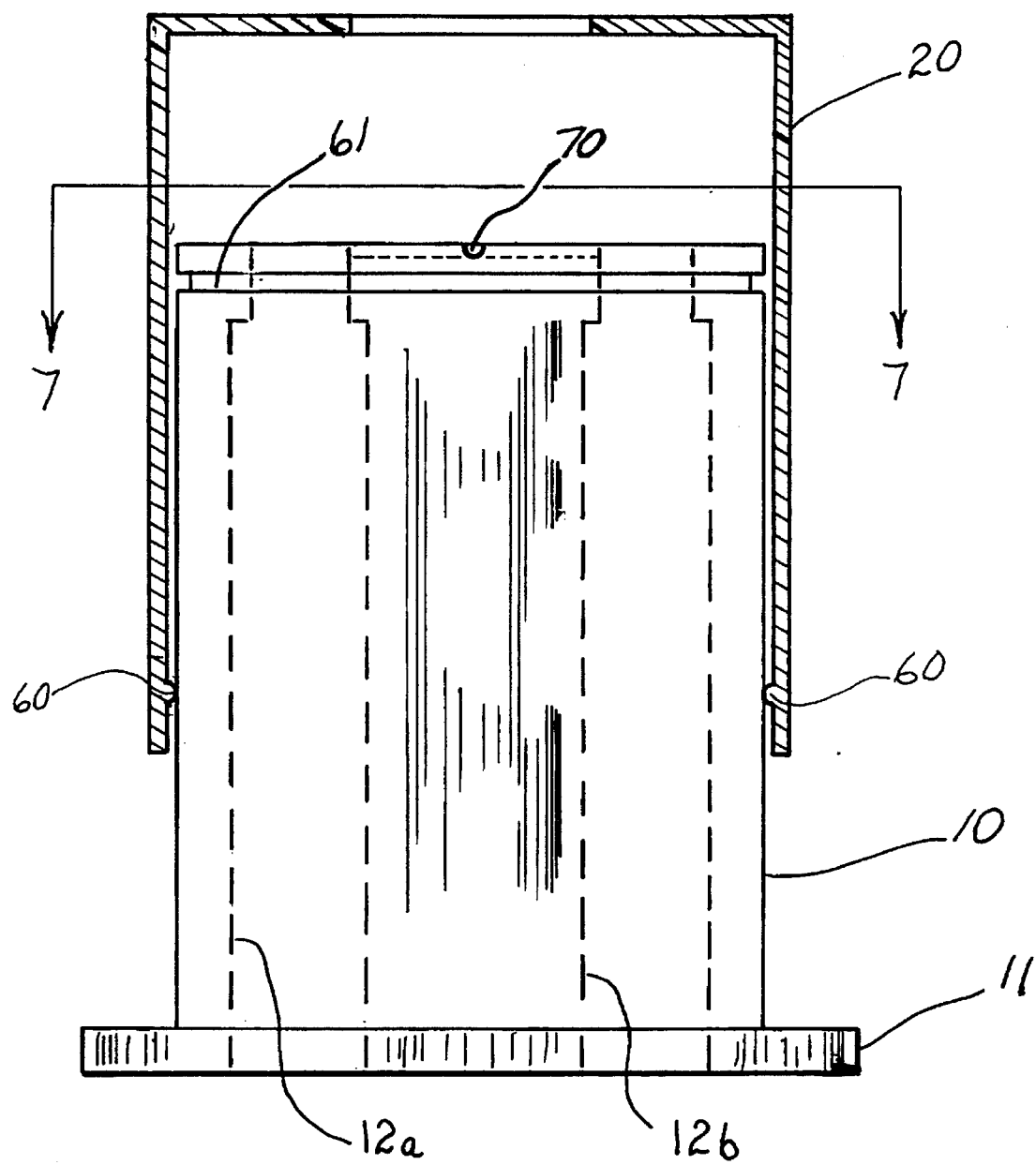
FIG. 6 is a side view in cross section of a blood sample tube holder showing the protective sheath and the latching mechanism.

When the blood sample tubes 14 have filled to the desired point, the technician grasps the sample tube loader 24 and partially withdraws the blood sample tubes 14, thereby removing the blood sample filling needles 34 from stoppers 15 and stopping the flow of blood, as will be further described. In the rare situation were more blood samples are required than the number of sample tubes 14 which can be accommodated by the holder 10, the technician will grasp the sample tube loader 24, fully withdraw the sample tubes 14 from the blood sample tube holder 10, and reload the sample tube holder 10 with a second sample tube loader 24 and blood sample tubes 14, forcing the sample tubes 14 fully into the blood sample tube holder 10 to reinitiate the flow of blood into the second set of sample tubes 14. Alternatively, if no additional blood samples are required, the technician grasps the sample tube loader 24 and partially withdraws it from sample tube holder 10 to stop the flow of blood. The venipuncture needle 16 is then withdrawn from the patient and the movable needle sheath 20 is moved outwardly, as shown in FIG. 6, to the protected position where it is protected from inadvertent contact by the patient, technician or others who may handle the blood sample tube holder 10.

Other significant aspects of the invention will now be described, beginning with FIG. 3, which is a partial sectional view of the device with the blood sample tubes 14 in the partially loaded position. The venipuncture needle 16 is retained by venipuncture needle collet 21 which screws into a threaded hole 22 in the manifold assembly 23. One arrangement of needle 16, collet 21 and manifold assembly is shown in FIG. 4. The primary manifold assembly 23 is made up of a molded outer housing 23a and complementary molded insert 23b. The molded outer housing 23a is joined to the molded insert 23b by any suitable means such as ultrasonic bonding, adhesive or a solvent weld. The outer housing 23a and insert 23b are designed to create a central chamber portion 29 of the blood distribution manifold 30 in the region where the second end 18 of venipuncture needle 16 disgorges the withdrawn blood. The dimensions and geometry of the central chamber portion 29 are selected to provide a laminar flow of the blood emerging from the second end 18 of needle 16. The central chamber portion 29 is symmetrically positioned about the second end 18 of venipuncture needle 16. Chamber 29 has a round interior wall. For needles of 0.5 to 2.0 mm diameter, chamber 29 has an internal diameter of 2.0 mm to 4.0 mm in the region adjacent to second end 18 of needle 16 to provide laminar flow of the blood emerging from end 18 of needle 10. This minimizes the damage to red blood cells.

To further minimize the mechanical damage to the red blood cells and to evenly divide the flow of blood into the individual blood sample tubes, chamber 29 includes a blood flow divider 32 positioned directly opposite, and spaced from, the open second end 18 of needle 16. The tip 32a of blood flow divider 32 has a spherical shape of not less than 0.5 mm diameter. The size and shape of tip 32a are selected to reduce the damage to red blood cells due to impact on the tip and to maintain laminar flow of blood in the blood distribution manifold 30.

Figure 4:
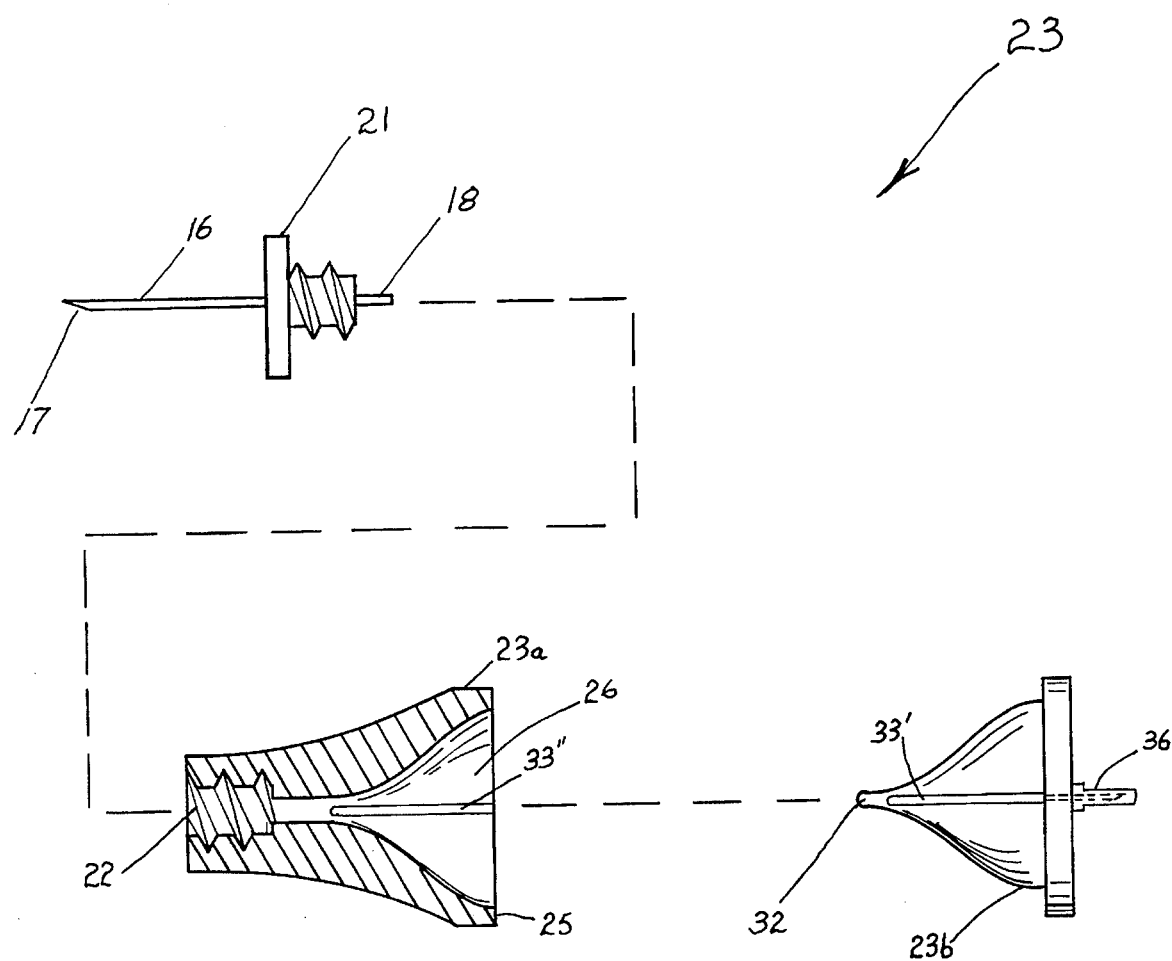
FIG. 4 is a exploded side view in partial cross section of a venipuncture needle incorporated into a portion of a venipuncture needle assembly for use with the blood sample collection device according to the invention.
Figure 5:
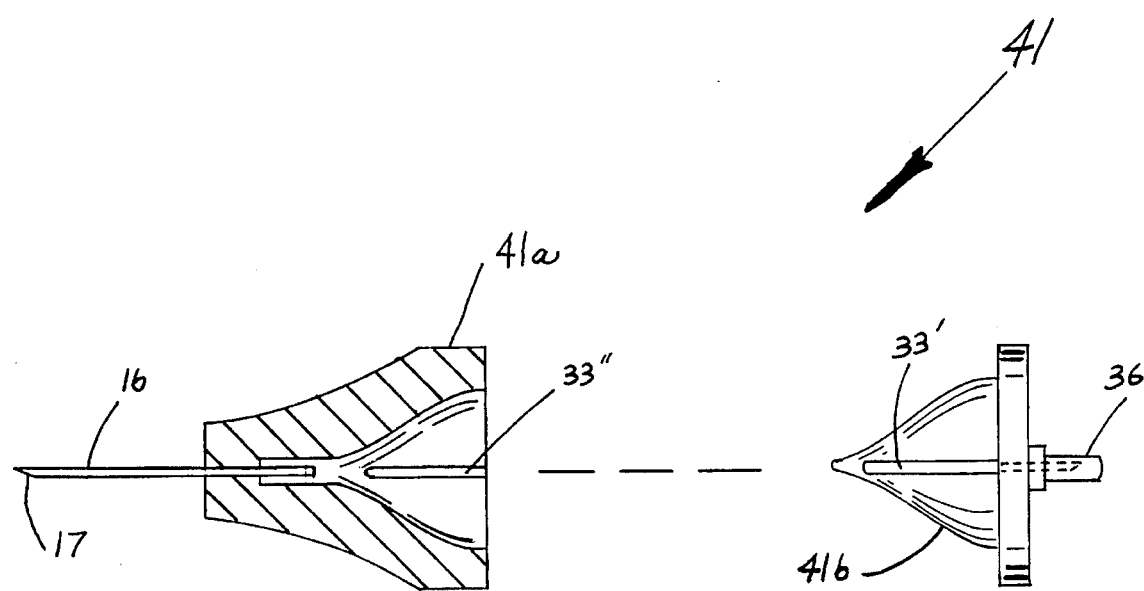
FIG. 5 is an exploded side view in partial cross section of an alternative venipuncture needle assembly for use with the blood sample collection device according to the invention.

An alternate manifold assembly is shown in FIG. 5. In this embodiment, the venipuncture needle 16 is molded in the outer housing 41a and becomes an integral part thereof. The complementary molded insert 41b has the same conforming shape as the insert 41b and performs the same function. Outer housing 41a and complementary insert 41a are fastened to each other in the same fashion as previously described with reference to FIG. 4.

Central chamber portion 29 of manifold 30 branches symmetrically into a plurality of curved individual passageways 33 leading downwardly to the sample tube filling needles 34 which have first ends 34a for piercing the elastomeric sample tube stopper 14 and second ends 34b centrally positioned within the respective lower regions 35 of passageways 33.

Referring again to FIG. 3, the manifold assembly 23 is joined to the blood sample tube holder 10 by suitable means such as ultrasonic bonding, adhesive or a solvent weld. Sample tube holder 10 includes a plurality of apertures 12, symmetrically arranged about the axis of tube 10, having an interior dimension and shape such that blood sample tubes 14 slide easily into the apertures.

Figure 3:
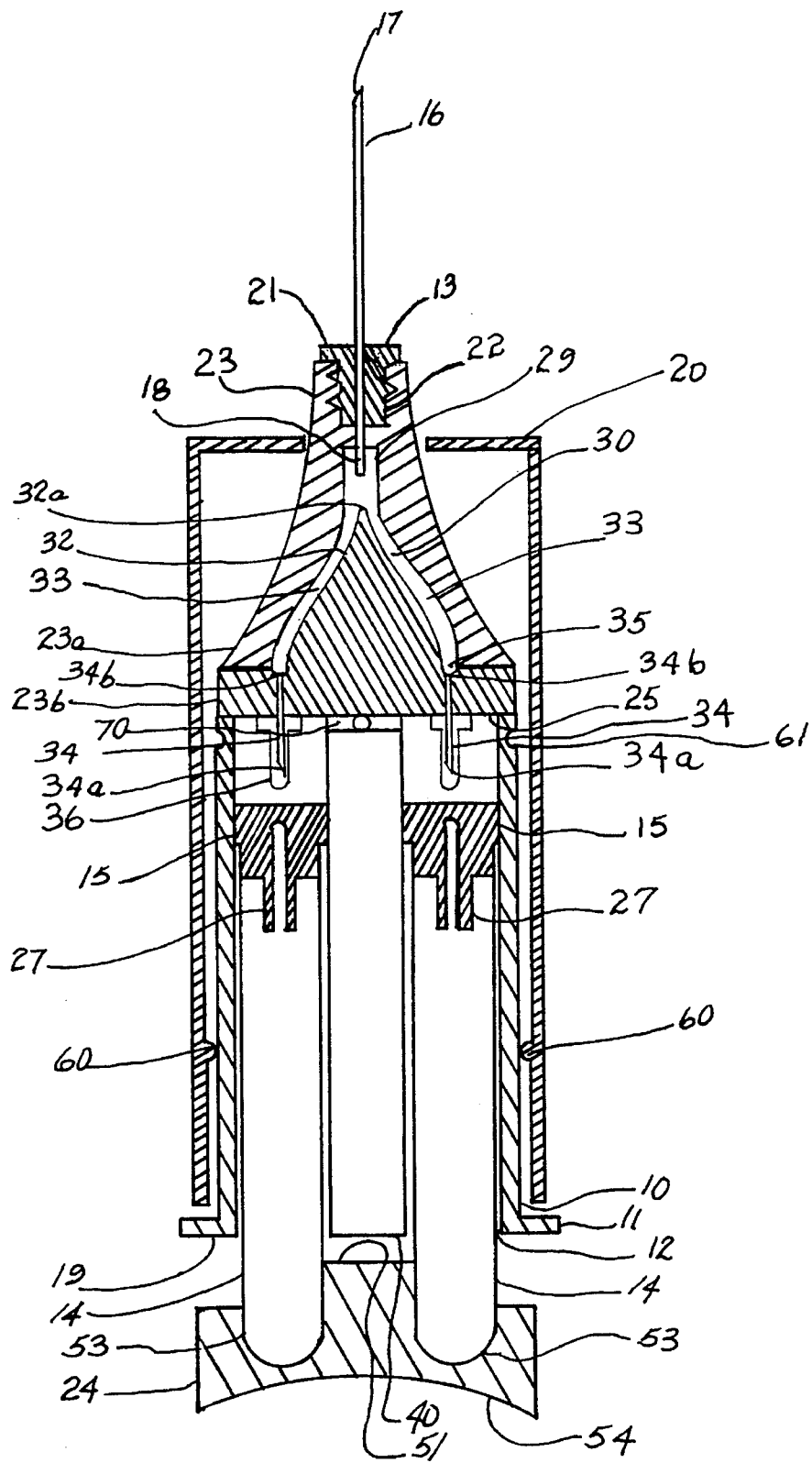
FIG. 3 is a side, partial sectional, view with the multiple sample tubes in position to be filled with blood.

The partially inserted position of sample tubes 14, as shown in FIG. 3, is just prior to the piercing of blood sample tube stopper 15 by sample tube filling needles 34. Each of the first ends 34a of sample tube filling needles 34 is covered with an elastomeric nipple 36, secured to the lower face 25 of manifold assembly 23 which serves to prevent the flow of blood from needles 34 until pierced. Further movement of the sample tubes 14 into sample tube holder 10 causes the end 34a of sample tube filling needle 34 to pierce elastomeric nipples 36 and then to pierce blood sample tube stoppers 15. When the blood sample tubes 14 are fully inserted into sample tube holder 10, the end 34a of sample tube filling needle 34 is centrally positioned within the laminar flow extender portion 27 of the elastomeric blood sample tube stoppers 15.

Laminar flow extender 27 is a centrally positioned tubular projection on the lower face of stopper 15. The projection extends approximately 5.0–15.0 mm beyond the end 34a of needle 34 and has a nominal interior diameter approximately 3.0–5.0 mm for use with sample tube filling needles of 1.3 mm diameter. The dimensions of laminar flow extender 27 are selected to preserve the laminar flow of blood into sample tubes 14, thereby avoiding mechanical hemolysis which would otherwise result from the impact of blood against the walls of sample tube 14.

A flange portion 11, at the bottom of blood sample tube holder 10, assists the technician in manipulating the device as well as providing a stop which prevents the movable needle sheath 20 from sliding off the device. Blood sample tube holder 10 further includes an axially located stop portion 40 which engages a correspond stop portion 51 on blood sample tube loader 24 and serves to limit the distance to which the blood sample tubes 14 may be inserted into apertures 12. This prevents overcompression of the elastomeric nipples 36 which might cause them to fail to properly reseal when the blood sample tubes 14 are withdrawn.

The multiple, symmetrically arranged, sample tube cavities 53 in elastomeric or flexible sample tube loader 24 are dimensioned to provide a tight fit on the ends of sample tubes 14. The sample tube cavities 53 have a sufficient internal surface area to maintain a friction fit with tubes 14 and thereby ensure that the sample tube loader 24 will successfully remove all the tubes 14 from the sample tube holder 10 when the loader 24 is withdrawn. The lower face 54 of sample tube loader 24 provides the technician with a convenient location for the application of force to pierce nipples 36 and sample tube stoppers 15.

Application of the loading and withdrawal force to sample tube loader 24, instead of directly to sample tubes 14, solves numerous problems. First, is ensures that all sample tubes 14 will be filled simultaneously, avoiding the situation where some tubes would only be partially filled. Second, it allows the technician to avoid direct contact with sample tubes 14 and prevents injury and possible infection should the sample tubes 14 inadvertently fracture. The loader 24 also accommodates the placement of the stop 51 which prevents inadvertent over compression of the nipples 36 by the technician. Finally, it allows the use of smaller blood sample tubes than are now in common use.

It has long been recognized that the existing, conventional, blood sample tubes having a nominal 13 mm diameter and 75 mm length to provide a blood sample of approximately 4.5 cc, are literally hundreds of times larger than need be to collect sufficient blood for analytical purposes. However, because smaller tubes, including the smaller, less common, tube having a nominal 10 mm diameter and 60 mm length, are difficult for the technician to manipulate while withdrawing blood, the use of the now oversized blood sample tubes has continued. The use of the blood sample tube loader 24 allows the technician to conveniently manipulate a much smaller blood sample tube with the attendant advantages previously discussed. The device of this invention can easily accommodate blood sample tubes in the range from 4 mm to 13 mm in diameter and 66 mm to 75 mm in length. Preferable, the blood sample tubes for use with this invention have a nominal diameter of 6 mm and a nominal length of 75 mm, which accommodates a blood sample of 2 cc.

FIG. 4 is an exploded side view in partial cross section of a venipuncture needle 16 incorporated into the manifold assembly 23 including the molded outer housing 23a, the manifold insert 23b and their associated components where all numerals correspond to those elements previously described. Illustrated in particular is one of the passageway half members 33' of passageway 33 illustrated on one side of the conical shaped manifold insert 23b and a passageway half member 33" illustrated on one of the inside conical surfaces 26 of the molded outer housing 23a. The appropriate corresponding passage halfway members 33' and 33" align together to form passageways 33 as illustrated in FIG. 3.

FIG. 5, an alternate embodiment, is an exploded view in partial cross section of a venipuncture needle 16 molded or otherwise permanently secured into the distal end of a manifold assembly 41 including a molded outer housing 41a, the manifold insert 41b and their associated components where all numerals correspond to those elements previously described. The passageways 33 are formed as described in FIG. 4.

FIG. 6 shows the details in cross section of the movable venipuncture needle sheath 20 which is designed to be used when the needle 16 is withdrawn from the patient. The interior cylindrical surface of sheath 20 has a diameter which provides an interference fit over the exterior surface of the sample tube holder 10. A plurality of latch projections 60 bear against the exterior of the sample tube holder 10 and provide the desired interference fit. When the sheath 20 is moved outwardly to the protected position the projections 60 snap into the annular groove 61 (FIG. 3) in sample tube holder 10 to hold the sheath 20 in the extended, protective position. Since the annular groove 61 extends completely around the sample tube holder 10, the needle sheath 20 will lock in the protective position regardless of its rotational position relative to sample tube holder 10.

Figure 7:
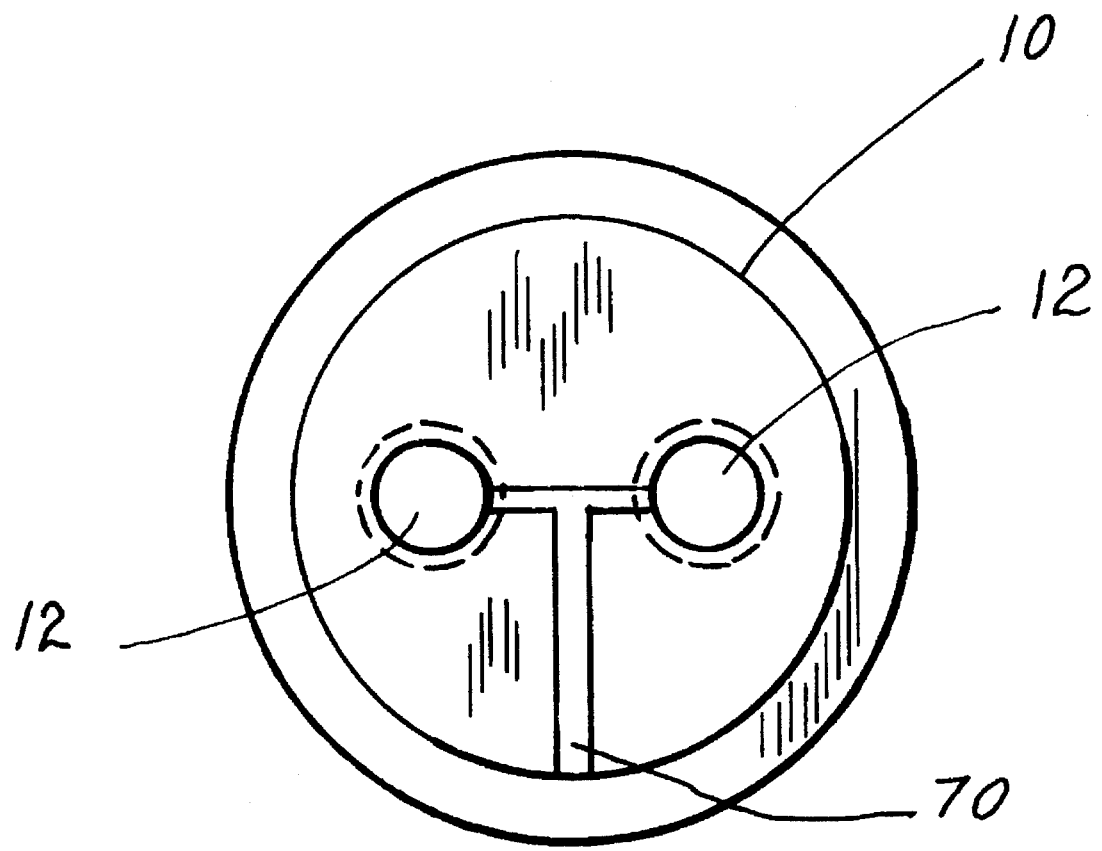
FIG. 7 is a top view of a blood sample tube holder along line 7—7 of FIG. 6 showing two apertures for accommodation of two blood sample tubes and a relief passage.

FIG. 7 is a top view of the two-tube sample tube holder along view line 7—7 of FIG. 6 showing the two apertures 12 for sample tubes and the air passage 70 which allows air to escape when the sample tubes 14 are forced into the sample tube holder 10 where all numerals correspond to those elements previously described. The air passages 70 aligns in the top of the sample tube holder 10.

Figure 8:
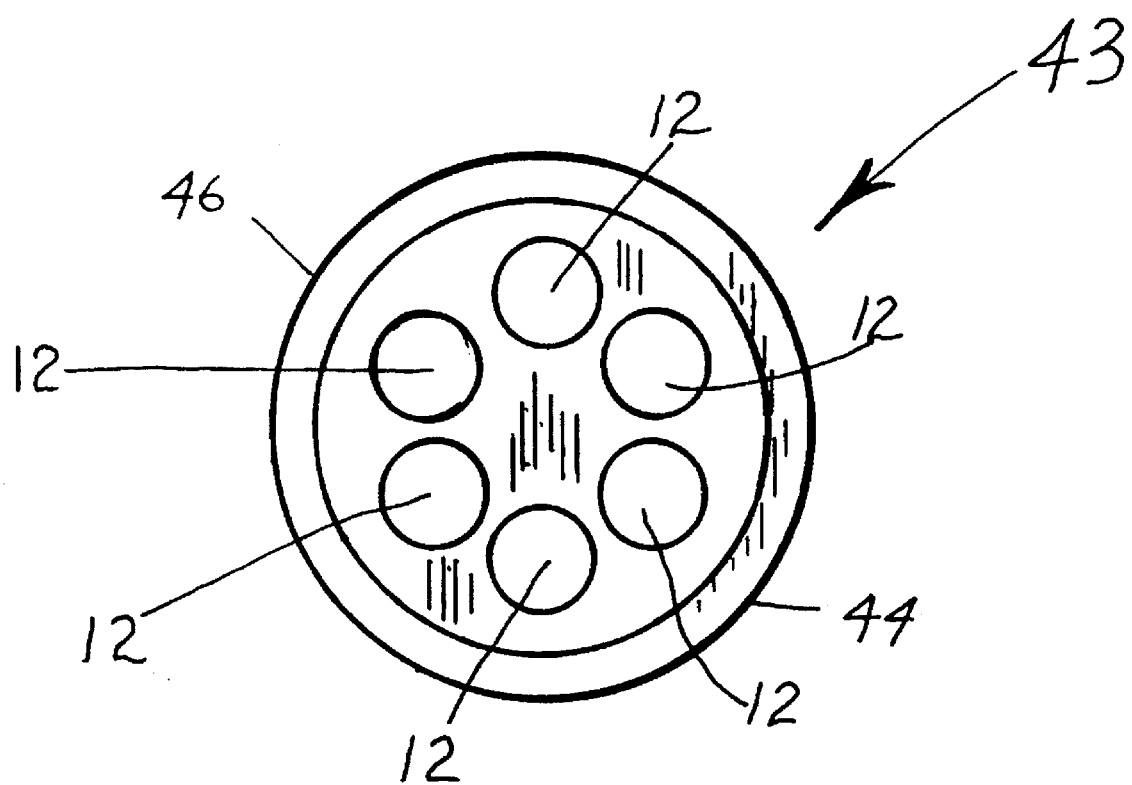
FIG. 8 is a bottom view of a blood sample tube holder showing 6 cylindrical apertures symmetrically arranged for accommodation of six blood sample tubes.

FIG. 8 is a bottom view of a sample tube holder having a flange 44 and six like apertures 12 designed to accommodate 6 sample tubes 14. Any number of apertures can be used to accommodate a like number of corresponding aligned sample tubes.

Figure 9:
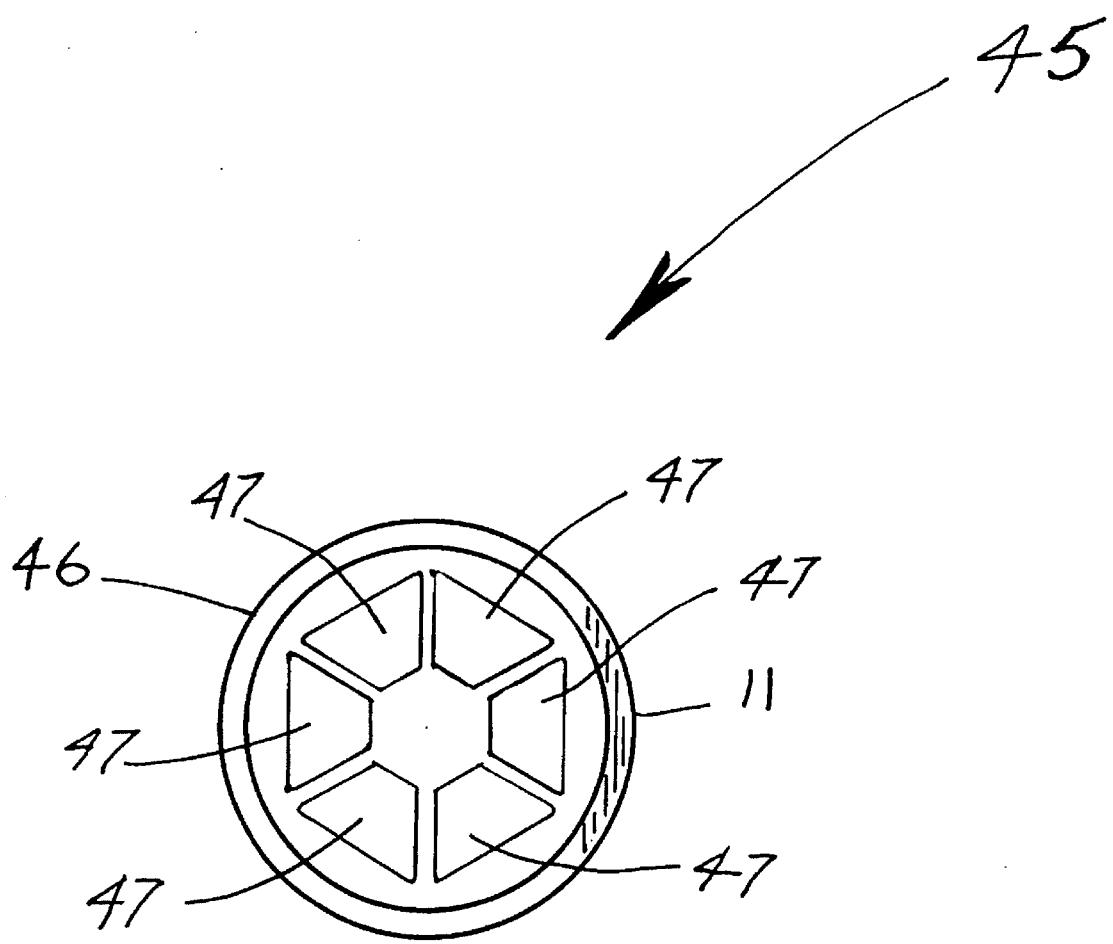
FIG. 9 is a bottom view of a blood sample tube holder showing 6 non-cylindrical apertures symmetrically arranged for accommodation of six non-cylindrical profile blood sample tubes.

FIG. 9 is a bottom view of a sample tube holder 45 having a flange 46 which is designed to accommodate triangular shaped sample tubes and having a plurality of triangular shaped apertures 47. It can be seen that the holder diameter can be reduced by using sample tubes of non-cylindrical cross section.

Figure 10:
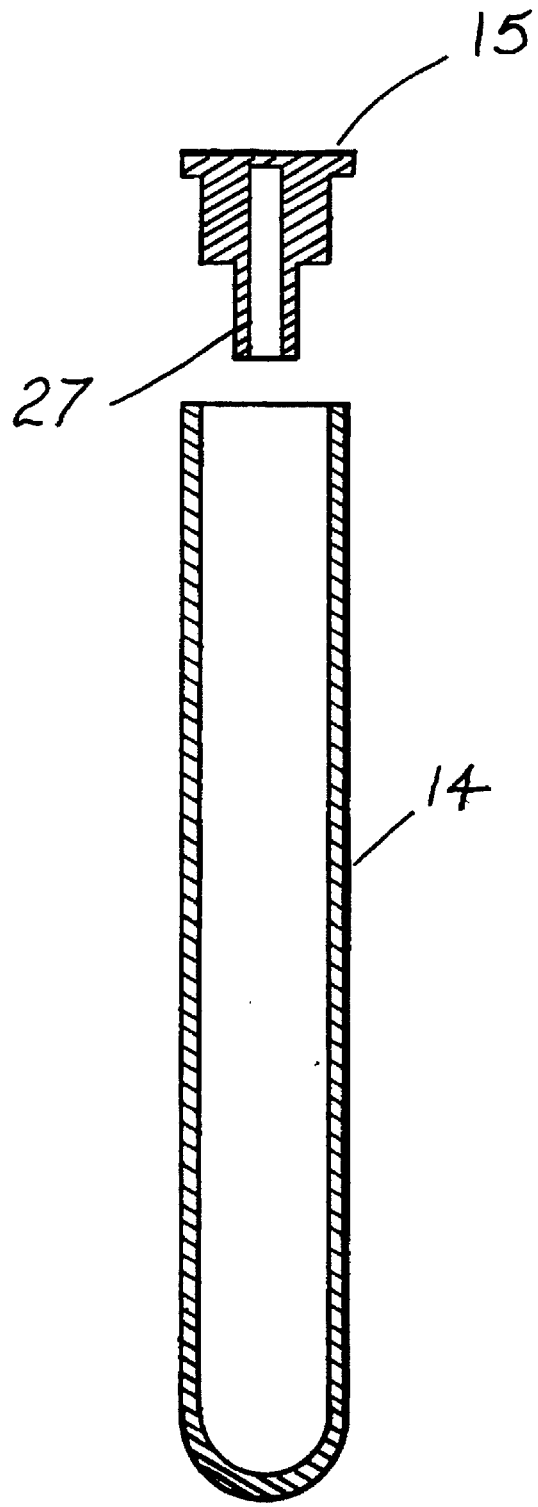
FIG. 10 is an exploded side view in cross section of a cylindrical blood sample tube illustrating the stopper and laminar flow extender.

FIG. 10 is an exploded cross section view of the round sample tube 14 for use with this invention showing the sample tube stopper 15 with the laminar flow extender 27.

Figure 11:
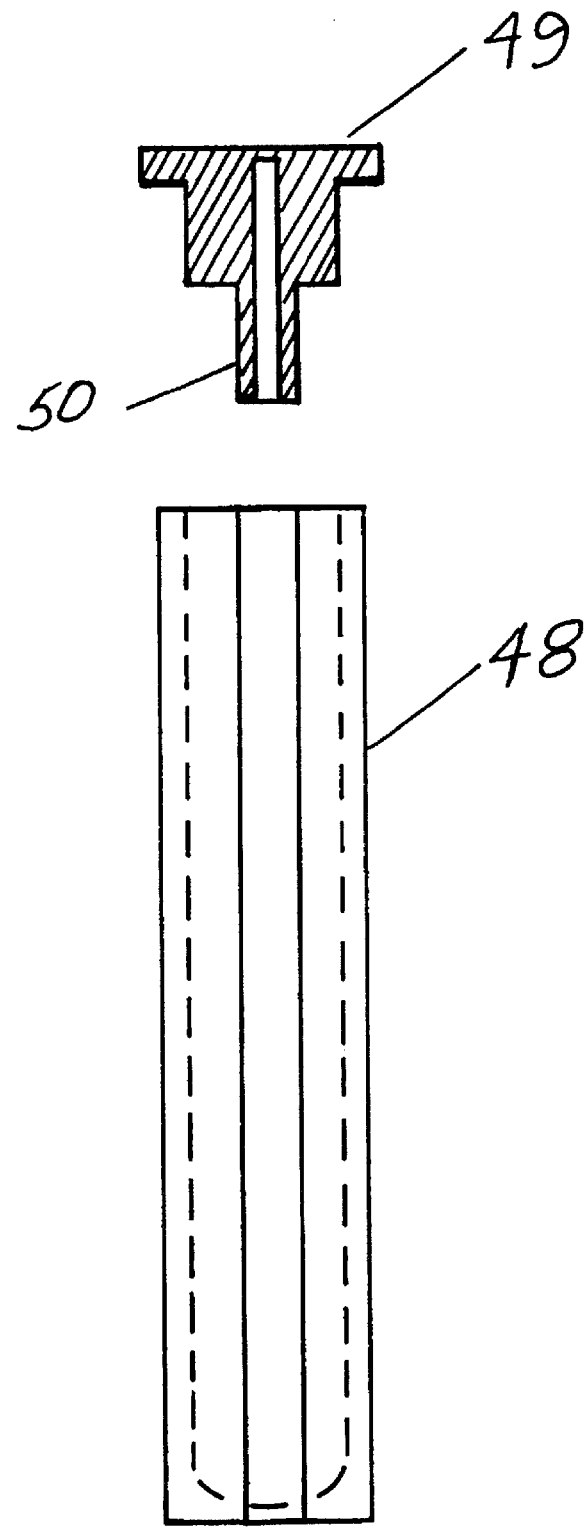
FIG. 11 is an exploded side view of a noncylindrical blood sample tube illustrating the stopper and laminar flow extender.

FIG. 11 is an exploded view of an alternative blood sample tube 48, having for purpose of example and illustration, an equilateral triangular shaped cross section of 1.4 mm on a side and a nominal length of 40 mm to provide a capacity of 1.96 cc. A triangular shaped elastomeric stopper 49 includes a laminar flow extender 50.

Figure 12:
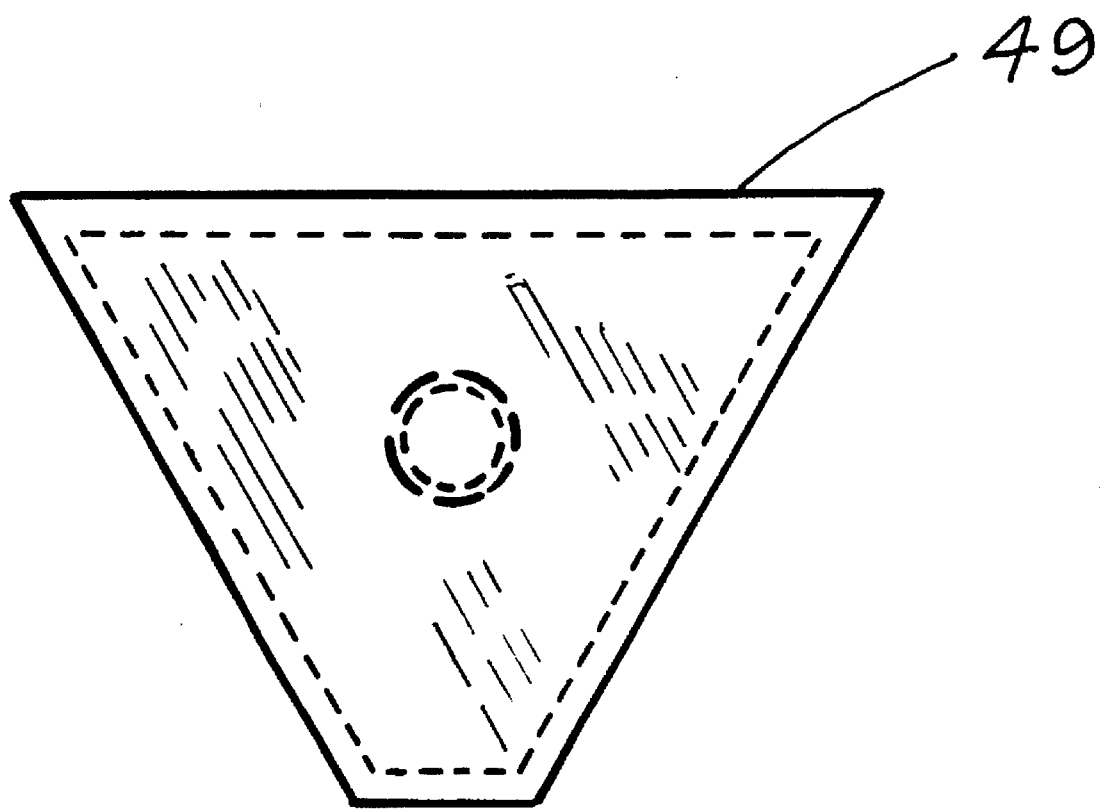
FIG. 12 is a top view of a stopper for the noncylindrical blood sample tube of FIG. 11.

FIG. 12 is a top view of the triangular stopper 49 for use with the triangular shaped blood sample tube 48 of FIG. 1.

MODE OF OPERATION

The multiple tube perfusion sampler of this invention is readied for use by grasping the blood sample tube loader 24 and partially inserting a plurality of blood sample tubes 14 into the apertures 12. The phlebotomist then inserts the first end 17 of the venipuncture needle 16 into the vein of the patient. When suitable placement of the needle 16 in the vein has been achieved, sufficient manual pressure is applied to the base 54 of the sample tube loader 24 to force the sample tube filling needles 34 through the elastomeric nipples 36 and sample tube stoppers 15 until the sample tube loader stop portion 51 comes to bear against the corresponding stop portion 40 on sample tube holder 10. The desired manual pressure is easily achieved without disturbing the placement needle 16 within the vein since flange 11 provides a secure grip on holder 10 and the phlebotomist need not worry about damaging the nipples 36 with over pressure.

When the sample tube filling needles emerge from the inner surface of blood sample tube stoppers 15, the pressure differential between the vein and the evacuated blood sample tube 14 causes venous blood to flow from the pierced vein through the interior of venipuncture needle 16 to the central chamber 29 of blood distribution manifold 30 where the flow is smoothly divided into the individual passageways 33 leading to the blood sample tube filling needles 34 and the laminar flow extender portion 27 of blood sample tube stoppers 15. The Bernoulli flow energy leveling provided by the laminar flow arrangement of the manifold chamber 30 and laminar flow extender portion 27 of blood sample tube stoppers 15 inhibits mechanical hemolysis which would damage the blood sample.

The blood sample tubes 14 fill at the same rate since any differential in pressure due to unequal flow causes a corrective, equalizing flow to the blood sample tubes.

When the blood sample tubes 14 have filled to the desired level, the blood sample tube loader 24 is withdrawn from the sample tube holder 10 a distance sufficient to retract the sample tube filling needles 34 from the stoppers 15 and restore them to the position within nipples 36, thereby effectively resealing the device and stopping the flow of blood. The needle 16 is then withdrawn from the vein of the patient and the protective sheath 20 is slid into the extended and locked position. Depending on the desired procedure, the plurality of filled sample tubes 14 may be withdrawn with the loader and sent to the laboratory or, alternatively, the entire device may be sent to the laboratory for blood analysis and subsequent disposal.

Various modifications can be made to the present invention without departing from the apparent scope hereof.

We claim:

1. A multiple sample blood collection device comprising;
   a. an elongated, generally cylindrical, blood sample tube holder having first and second ends, said first end including a plurality of apertures symmetrically disposed about the central axis of said tube holder and adapted to receive individual evacuated blood sample tubes;
   b. a venipuncture needle positioned in said second end coaxially positioned on said central axis of said holder, said venipuncture needle having a first end for insertion into the body from which blood is to be drawn and a second end positioned within said tube holder;
   c. a sample tube filling needle positioned within each of said apertures in said tube holder and having a first end for insertion into an evacuated sample tube and a second end for receiving blood from said venipuncture needle;
   d. an elastomeric nipple affixed to said sample tube holder and positioned over said first end of said sample tube filling needle to prevent flow of blood unless punctured by said first end of said sample tube filling needle when said first end is inserted into an evacuated sample tube;
   e. a manifold chamber connecting said second end of said venipuncture needle and said second ends of each of said sample tube filling needles;
   f. said manifold chamber comprising a central chamber portion symmetrically arranged with respect to said second end of said venipuncture needle and a plurality of sample tube filling passages branching therefrom in symmetrical relationship whereby laminar flow of blood is maintained during transfer of blood from second end of said venipuncture needle to said second end of said sample tube filling needle to minimize the damage to red blood cells during blood sample collection;

g. a loader for multiple sample tubes, and a first end of said loader having a plurality of sample tube cavities therein, each said sample tube cavity being arranged for alignment with a corresponding one of said plurality of apertures in said blood sample tube holder;

h. wherein said sample tube loader includes a second end, opposite said first end, for the application of force to move sample tubes held therein into said plurality of apertures and cause said first ends of said sample tube filling needles to puncture said elastomeric nipples and plugs in the open ends of sample tubes; and, i. wherein said sample tube loader has a centrally positioned stop portion on said first end adapted to engage said sample tube holder and limit the distance to which said sample tubes may be inserted into said holder.

2. A multiple sample tube blood collection device according to claim 1 wherein said sample tube cavities in said sample tube loader have an inner dimension slightly less than the outer dimension of said sample tubes whereby said sample tubes are held with said loader by frictional force.

3. A multiple sample blood collection device according to claim 1 wherein said manifold includes a blood flow divider opposite said second end of said venipuncture needle and centrally positioned within the stream of blood emerging from said venipuncture needle at a distance approximately ten times the internal diameter of said venipuncture needle.

4. A multiple sample blood collection device according to claim 3 wherein said blood flow divider is of generally conical shape.

5. A multiple sample blood flow collection device according to claim 4 wherein said conical blood flow divider terminates in a spherical shape having a diameter between 0.5 mm and 1.0 mm.

6. A multiple blood sample blood collection device according to claim 1 wherein each of said manifold sample tube filling passages have a curved diverging portion extending from said blood flow divider and a curved axial alignment portion extending to said second end of said sample tube filling needle whereby laminar flow of blood is maintained throughout said manifold.

7. A multiple blood sample blood collection device according to claim 1 adapted for use with sample tubes having a nominal diameter less than 13 mm and a nominal length of less than 75 mm.

8. A multiple sample blood collection device comprising:

a. an elongated, substantially cylindrical, blood sample tube holder having first and second ends, said first end including a plurality of apertures symmetrically disposed about the central axis of said tube holder and adapted to receive individual evacuated blood sample tubes having an external diameter of less than 8 mm;

b. a venipuncture needle positioned in said second end coaxially positioned on said central axis of said holder, said venipuncture needle having a first end for insertion into the body from which blood is to be drawn and a second end positioned within said tube holder;

c. a sample tube filling needle positioned within each of said apertures in said tube holder and having a first end for insertion into an evacuated sample tube and a second end for receiving blood from said venipuncture needle;

d. an elastomeric nipple affixed to said sample tube holder and positioned over said first end of said sample tube filling needle to prevent flow of blood unless punctured by said first end of said sample tube filling needle when said first end is inserted into an evacuated sample tube;

e. a manifold chamber connecting said second end of said venipuncture needle and said second ends of each of said sample tube filling needles;

f. said manifold chamber comprising a central chamber portion symmetrically arranged with respect to said second end of said venipuncture needle and a plurality of sample tube filling passages branching therefrom in a symmetrical relationship whereby laminar flow of blood is maintained during the passage of blood from second end of said venipuncture needle to said second end of said sample tube filling needle to minimize the damage to blood cells during the blood sample collection procedure;

g. a loader for simultaneously inserting multiple sample tubes into said holder;

h. a first end of said loader having a plurality of sample tube cavities therein, each said sample tube cavity having an internal diameter less than 8 mm and arranged for alignment with a corresponding one of said plurality of apertures in said blood sample tube holder;

i. a loader for multiple sample tubes, and a first end of said loader having a plurality of sample tube cavities therein, each said sample tube cavity being arranged for alignment with a corresponding one of said plurality of apertures in said blood sample tube holder; and, j. wherein said sample tube loader has a centrally positioned stop portion on said first end adapted to engage said sample tube holder and limit the distance to which said sample tubes may be inserted into said holder.

9. A multiple sample blood collection device according to claim 8 wherein said sample tube loader includes a second end, opposite said first end, for the application of force to move sample tubes held therein into said plurality of apertures and cause said first end of said sample tube filling needles to puncture plugs in the open ends of said sample tubes.

10. A multiple sample tube blood collection device according to claim 8 wherein said sample tube cavities in said sample tube loader have an inner dimension slightly less than the outer dimension of said sample tubes whereby said sample tubes are held with said loader by frictional force.

11. A multiple sample blood collection device according to claim 8 wherein said manifold includes a blood flow divider opposite said second end of said venipuncture needle and centrally positioned within the stream of blood emerging from said venipuncture needle at a distance approximately ten times the internal diameter of said venipuncture needle.

12. A multiple sample blood collection device according to claim 11 wherein said blood flow divider is of generally conical shape.

* * * * *